Figure 1:
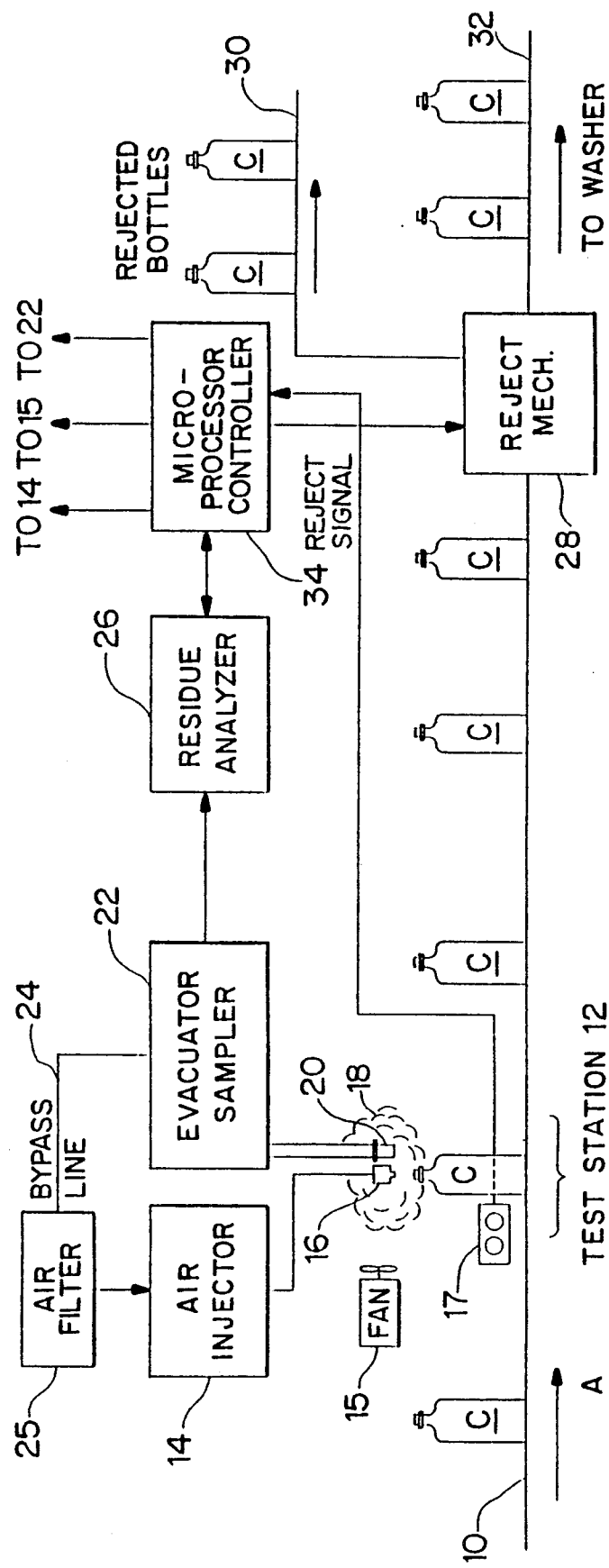

United States Patent [19]

Fine et al.

[11] Patent Number: 5,318,911
[45] Date of Patent: Jun. 7, 1994

[54] SYSTEM FOR SAMPLING AND DETERMINING THE PRESENCE OF COMPOUNDS IN CONTAINERS

[75] Inventors: David H. Fine, Sudbury; Freeman W. Fraim, Lexington, both of Mass.; Stephen J. MacDonald, Salem, N.H.; Kenneth M. Thrash, Jr., Decatur, Ga.

[73] Assignee: The Coca-Cola Company, Atlanta, Ga.

[21] Appl. No.: 49,337

[22] Filed: Apr. 21, 1993

Related U.S. Application Data

[62] Division of Ser. No. 890,863, Jun. 1, 1992.

[51] Int. Cl.$^5$ .................. G01N 35/02; G01N 21/88; G01N 21/76
[52] U.S. Cl. ...................... 436/47; 436/43; 436/106; 436/172; 422/82.05; 422/82.08; 422/83
[58] Field of Search ............. 436/47, 43, 106, 172; 422/82, 82.05, 82.08, 83, 104; 73/23.35, 23.41

[56] References Cited

U.S. PATENT DOCUMENTS

| | | | |
|---|---|---|---|
| 1,934,808 | 11/1933 | Liptay | 422/104 |
| 1,972,917 | 9/1934 | Buckel | 422/104 |
| 3,713,785 | 1/1973 | Moran | 422/104 |
| 3,763,877 | 10/1973 | Lieb | 137/117 |
| 3,845,309 | 10/1974 | Helm et al. | 250/365 |
| 4,193,963 | 3/1980 | Bruening | 422/52 |
| 4,257,777 | 3/1981 | Dymond et al. | 422/52 |
| 4,265,855 | 5/1981 | Mandle et al. | 422/65 |
| 4,580,440 | 4/1986 | Reid et al. | 73/31.07 |
| 4,775,633 | 10/1988 | Rounbehler | 436/111 |
| 4,830,192 | 5/1989 | Plester et al. | 209/3.1 |
| 4,843,016 | 6/1989 | Fine | 436/172 |
| 4,858,768 | 8/1989 | Plester | 209/3.1 |
| 4,880,120 | 11/1989 | Myers et al. | 209/3.1 |
| 4,909,089 | 3/1990 | Achter et al. | 73/863.1 |
| 4,909,090 | 3/1990 | McGown et al. | 73/864.33 |
| 5,067,616 | 11/1991 | Plester et al. | 209/3.1 |
| 5,108,705 | 4/1992 | Rounbehler et al. | 422/89 |
| 5,152,963 | 10/1992 | Wreyford | 422/80 |

*Primary Examiner*—James C. Housel
*Assistant Examiner*—Rachel Heather Freed
*Attorney, Agent, or Firm*—Birch, Stewart, Kolasch & Birch

[57] ABSTRACT

A method and apparatus for sampling and determining the presence of certain substances, such as residues of contaminants in containers. The method includes steps of: injecting compressed air into said containers in order to displace at least a portion of the contents thereof; evacuating a sample of the container contents so displaced by applying suction thereto; and analyzing the sample evacuated to determine the presence or absence of the certain residues therein. The compressed air is injected through a nozzle into an opening in the containers to displace a portion of the container contents and form a sample cloud outside of the container. The sample cloud is then at least partially evacuated by suction and the sample is analyzed for the presence of contaminants such as nitrogen containing compounds or hydrocarbons. In one embodiment about 90% of the sample evacuated is diverted from the analyzer and recirculated into the air injector. In another embodiment a fan is provided to blow remnants of the sample cloud downstream of the test station. A hood may be provided in a shroud assembly at the test station to provide proper aerodynamics for the region for removal of those remnants.

26 Claims, 6 Drawing Sheets

SYSTEM FOR SAMPLING AND DETERMINING THE PRESENCE OF COMPOUNDS IN CONTAINERS

This application is a divisional of copending U.S. applicaiton Ser. No. 07/890,863, filed on Jun. 1, 1992, the entire contents of which are hereby incorporated by reference.

BACKGROUND OF THE INVENTION

The present invention relates to a an inspection system for sampling and determining the presence of certain substances, such as residues of contaminants within containers such as glass or plastic bottles. More specifically, the present invention relates to an improved sampling and analyzing system and method for determining the presence of substances such as residues of contaminants, as in containers such as beverage bottles rapidly moving along a conveyor past a test station in a container sorting system.

In many industries, including the beverage industry, products are packaged in containers which are returned after use, washed and refilled. Typically refillable containers, such as beverage bottles, are made of glass which can be easily cleaned. These containers are washed and then inspected for the presence of foreign matter.

Glass containers have the disadvantage of being fragile and, in larger volumes, of being relatively heavy. Accordingly, it is highly desirable to use plastic containers because they are less fragile and lighter than glass containers of the same volume. However, plastic materials tend to absorb a variety of organic compounds which may later be desorbed into the product thereby potentially adversely affecting the quality of the product packed in the container. Examples of such organic compounds are nitrogen containing compounds such as ammonia, organic nitrogen compounds, and hydrocarbons including gasoline and various cleaning fluids.

SUMMARY OF THE INVENTION

Accordingly, it is a primary object of the present invention to provide a method and system for detecting the presence or absence of specific substances—e.g., contaminants such as hydrocarbons, in materials as the materials move rapidly along a conveyor.

It is another object of the present invention to provide a system and method for sampling and analyzing residues in containers as they move along a conveyor without stopping the movement of the containers or impeding the movement in any way in order that high speed sampling rates of about 200 to 1000 bottles per minute may be achieved.

It is still another object of the present invention to provide a system and method for sampling and analyzing residues in containers moving along a conveyor without contacting the container being tested with any of the sampling and analyzing mechanisms.

It is yet another object of the present invention to provide a system and method for sampling and analyzing residues in containers moving along a conveyor without the physical insertion of any probes or the like into the containers.

The objects of the present invention are fulfilled by providing a method and apparatus for sampling and determining the presence of certain substances, such as volatile residues in containers. According to one embodiment of the invention, a method comprises the steps of: injecting fluid into said containers in order to displace at least a portion of the contents thereof; evacuating a sample of the container contents so displaced by applying suction thereto; and analyzing the sample evacuated to determine the presence or absence of the certain residues therein.

In a preferred embodiment the fluid injected into the containers is compressed air which is injected through a nozzle to provide an air blast within the interior of the container. This air blast creates a cloud of the vaporous contents of the container which emerges from its opening whereby it may be evacuated by suction from outside of the container to sample a portion of the container contents.

Injection of fluid and evacuation of sample may be continuous operations or may be performed in steps. If steps are utilized, the step of initiating the injection of fluid into the container preferably precedes in time the initiation of the step of evacuating a sample in order to provide time for the formation of the sample cloud. However, the performance of the steps of injecting and evacuating may slightly overlap in time. Alternatively, the steps of injecting and evacuation may be spaced in time but this is dependent on the rate of sampling desired. A still further alternative is to synchronize the steps of injecting and evacuating to occur simultaneously for the same duration.

In a preferred embodiment the injection of fluid from the nozzle and the suction applied by the evacuation means are continuously on at the test station. In this embodiment the containers or bottles are rapidly and continuously moved through the test station on a rapidly moving conveyor. The bottles are moved through the test station at a rate of 200 to 1000 bottles per minute. A rate of 400 bottles per minute is preferable and is compatible with current beverage bottle filling speeds. Of course the system will still work if the bottles are stationary, or moving at speeds below 200 bottles per minute. The desired test rate may vary with the size of the bottles being inspected and filled. The injector nozzle is disposed upstream of the direction of conveyor movement from the suction tube of the evacuator so the injection of fluid into each container slightly precedes in time the evacuation of the resulting sample cloud.

In another embodiment of the present invention a portion of the sample evacuated (about 90%) is diverted and the remaining portion of the sample passes to an analyzer for determination of the presence or absence of the certain residues. The purpose of diverting the first portion of the sample is to limit the amount of sample that passes to the analyzer to manageable quantities in order to achieve high speed analysis. In addition if the volume of the sample is too large it may foul or clog the detector. However, it is initially desirable to evacuate essentially the entire sample cloud to clear the area of the test station from the contents of that sample cloud to provide clean surroundings for the successive containers. This eliminates spurious carry over signals of residue (crosstalk of container contaminants) unrelated to the container being tested at a given point in time.

If desired the diverted portion of the first sample may be channeled through an optional air filter and recirculated into the compressed air being injected into subsequent containers to arrive at the test station. This provides for an efficient use of the diverted first portion of the sample and of a pump utilized for diversion and compression, and avoids the need to exhaust that first portion of the sample to the atmosphere surrounding the test site.

In a further embodiment a fan is provided to blow remnants of the sample cloud downstream of the test station. A hood may be provided over the test station to provide proper aerodynamics for the region.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus, are not limitative of the present invention and wherein:

FIG. 1 is a schematic block diagram of the sampling and residue analyzing system of the present invention illustrating a plurality of containers moving seriatim along a conveyor system through a test station, reject mechanism and washer station;

FIG. 1A is a schematic block diagram of a system similar to FIG. 1 with two test stations and detection heads;

FIG. 2 is a block diagram illustrating a possible implementation of the system of FIG. 1 in a detector system in which the contaminant being detected may be a nitrogen containing compound;

FIG. 3 is a front elevational view of a preferred form of the apparatus for use in the system and method of the present invention including a shroud partially enclosing system components and a sampling region above the test station along the conveyor;

FIG. 4 is a bottom perspective view of the shroud of FIG. 3;

FIG. 5 is a side elevational view in cross-section of the shroud of FIG. 3; and FIG. 6 is a partial cross-sectional view of the bottom wall of the shroud showing a louver assembly for directing a stream of air through the sample region in the direction of movement of the containers.

DETAILED DESCRIPTION OF PREFERRED EMBODIMENTS

Referring to FIG. 1 there is illustrated a conveyor 10 moving in the direction of arrow A having a plurality of uncapped, open-topped spaced containers C (e.g. plastic beverage bottles of about 1500 c.c. volume) disposed thereon for movement seriatim through a test station 12, reject mechanism 28 and conveyor 32 to a washer system. To achieve higher test rates containers C could be touching each other rather than spaced. The contents of containers C would typically include air, volatiles of residues of contaminants, if any, and volatiles of any products such as beverages which had been in the containers. An air injector 14 which is a source of compressed air is provided with a nozzle 16 spaced from but aligned with a container C at test station 12. That is nozzle 16 is disposed outside of the containers and makes no contact therewith. Nozzle 16 directs compressed air into containers C to displace at least a portion of the contents of the container to thereby emit a sample cloud 18 to a region outside of the container being tested.

As an alternative to compressed air, $CO_2$ gas could be utilized as the injected fluid. Also the compressed air or $CO_2$ gas could be heated to enhance volatility of the compounds being tested.

The column of injected air through nozzle 16 into a container C would be typically of the order of about 10 c.c. for bottle speeds of about 200 to 1000 bottles per minute. A rate of 400 bottles per minute is preferable and is compatible with current beverage bottle filling speeds. The desired test rate may vary with the size of the bottles being inspected and filled. Of course the bottles could be stationary or moving slower than 200 bottles per minute and the system would still work. Only about 10 c.c. of the container contents would be displaced to regions outside of the bottle to form sample cloud 18.

Also provided is an evacuator sampler 22 which may comprise a vacuum pump or the like coupled to a sampling tube or conduit 20. The tube is mounted near, and preferably downstream (e.g., about 1/16 inch) of the air injector 14 so as to be in fluid communication with sample cloud 18 adjacent to the opening at the top of containers C.

Neither nozzle 16 nor tube 20 contacts the containers C at test station 12; rather both are spaced at positions outside of the containers in close proximity to the openings thereof. This is advantageous in that no physical coupling is required to the containers C, or insertion of probes into the containers, which would impede their rapid movement along conveyor 10 and thus slow down the sampling rate. High speed sampling rates of from about 200 to 1000 bottles per minute are possible with the system and method of the present invention. The conveyor 10 is preferably driven continuously to achieve these rates without stopping or slowing the bottles down at the test station.

A bypass line 24 is provided in communication with the evacuator sampler 22 so that a predetermined portion (preferably about 90%) of the sample from cloud 18 entering tube 20 can be diverted through bypass line 24. The remaining sample portion passes to a residue analyzer 26, which determines whether specific substances are present, and then is exhausted. One purpose of diverting a large portion of the sample from cloud 18 is to reduce the amount of sample passing from evacuator sampler 22 to residue analyzer 26 in order to achieve high speed analysis. This is done in order to provide manageable levels of samples to be tested by the residue analyzer 26. Another purpose for diverting a portion of the sample is to be able to substantially remove all of sample cloud 18 by evacuator 22 from the test station area and divert the excess through bypass line 24. In a preferred embodiment the excess portion of the sample passing through bypass line 24 returned to air injector 14 for introduction into the subsequent containers moving along conveyor 10 through nozzle 16. However, it would also be possible to simply vent bypass line 24 to the atmosphere.

It should be understood that sample cloud 18 could be analyzed in situ without transporting it to a remote analyzer such as 26. It could also be transported to analyzer 26 by blowing rather than sucking.

A microprocessor controller 34 is provided for controlling the operation of air injector 14, evacuator sampler 22, residue analyzer 26, a reject mechanism 28 and an optional fan 15. Container sensor 17 including juxtaposed radiation source and photodetector is disposed opposite a reflector (not shown) across conveyor 10. Sensor 17 tells controller 34 when a container arrives at the test station and briefly interrupts the beam of radiation reflected to the photodetector. Optional fan 15 is provided to generate an air blast towards sample cloud 18 and preferably in the direction of movement of containers C to assist in the removal of sample cloud 18 from the vicinity of test station 12 after each container C is sampled. This clears out the air from the region of the test station so that no lingering residues from an existing sample cloud 18 can contaminate the test station area when successive containers C reach the test station for sampling. Thus, sample carryover between containers is precluded. The duty cycle for operation of fan 15 is controlled by microprocessor 34 as indicated diagrammatically in FIG. 1. Preferably fan 15 is continuously operating for the entire time the rest of the system is operating.

A reject mechanism 28 receives a reject signal from microprocessor controller 34 when residue analyzer 26 determines that a particular container C is contaminated with a residue of various undesirable types. Reject mechanism 28 diverts contaminated rejected bottles to a conveyor 30 and allows passage of uncontaminated, acceptable bottles to a washer (not shown) on a conveyor 32.

An alternative option is to place the bottle test station downstream of the bottle washer in the direction of conveyor travel, or to place an additional test station and sample and residue analyzing system after the washer. In fact it may be preferable to position the test station and system after the washer when inspecting bottles for some contaminants. For example, if the contaminant is a hydrocarbon, such as gasoline which is insoluble in water, it is easier to detect residues of hydrocarbons after the bottles have been washed. This is because during the washing process in which the bottles are heated and washed with water, water soluble chemical volatiles are desorbed from the bottles by the heating thereof and then dissolved in the washing water. Certain hydrocarbons, on the other hand, not being water soluble, may then be sampled by a sampler 22 downstream of the washer, to the exclusion of the dissolved, water- soluble chemicals. Therefore, the detection of such hydrocarbons can be performed without potential interference from other water soluble chemicals if the bottles pass through a washer before testing.

Figure 1A:
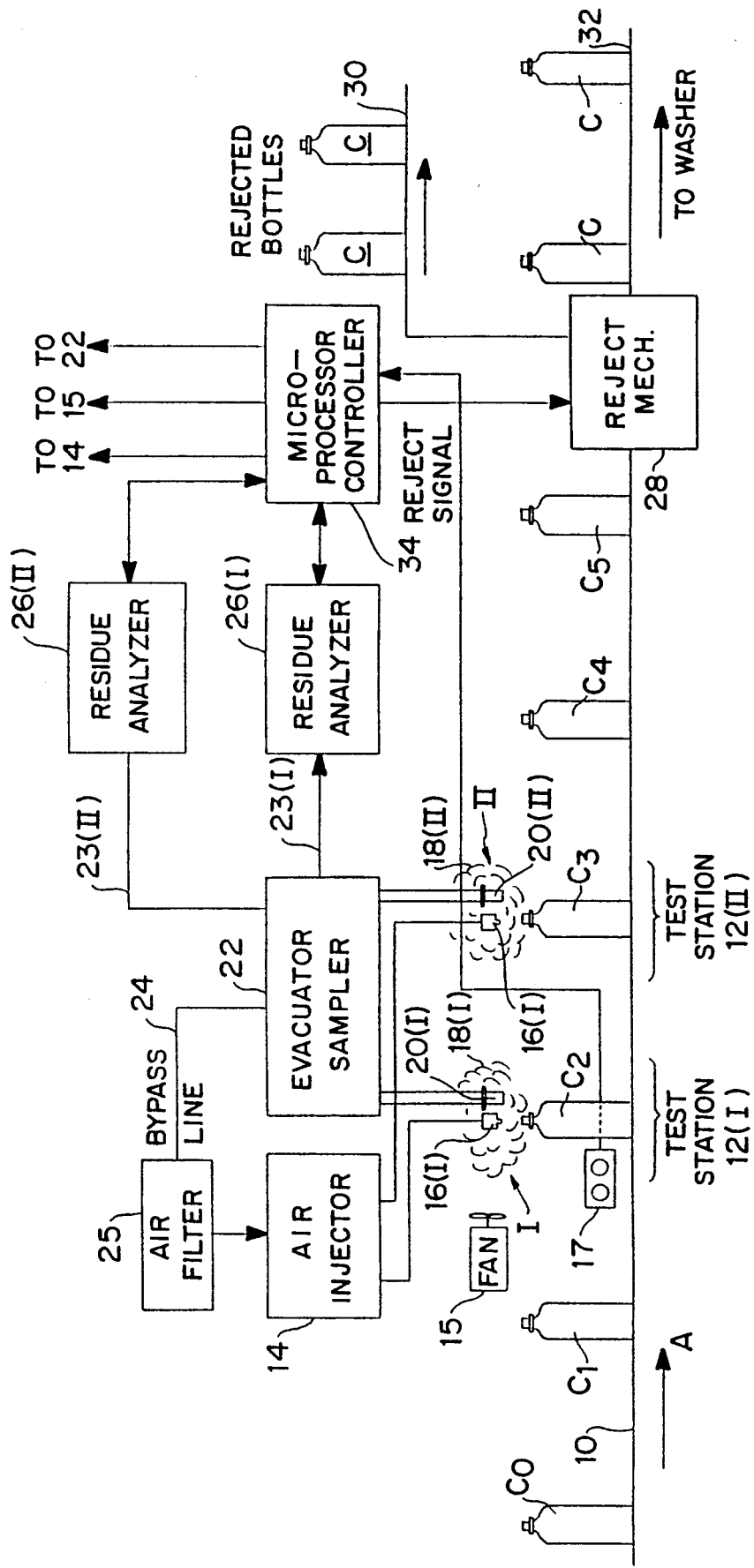
Figure 2:
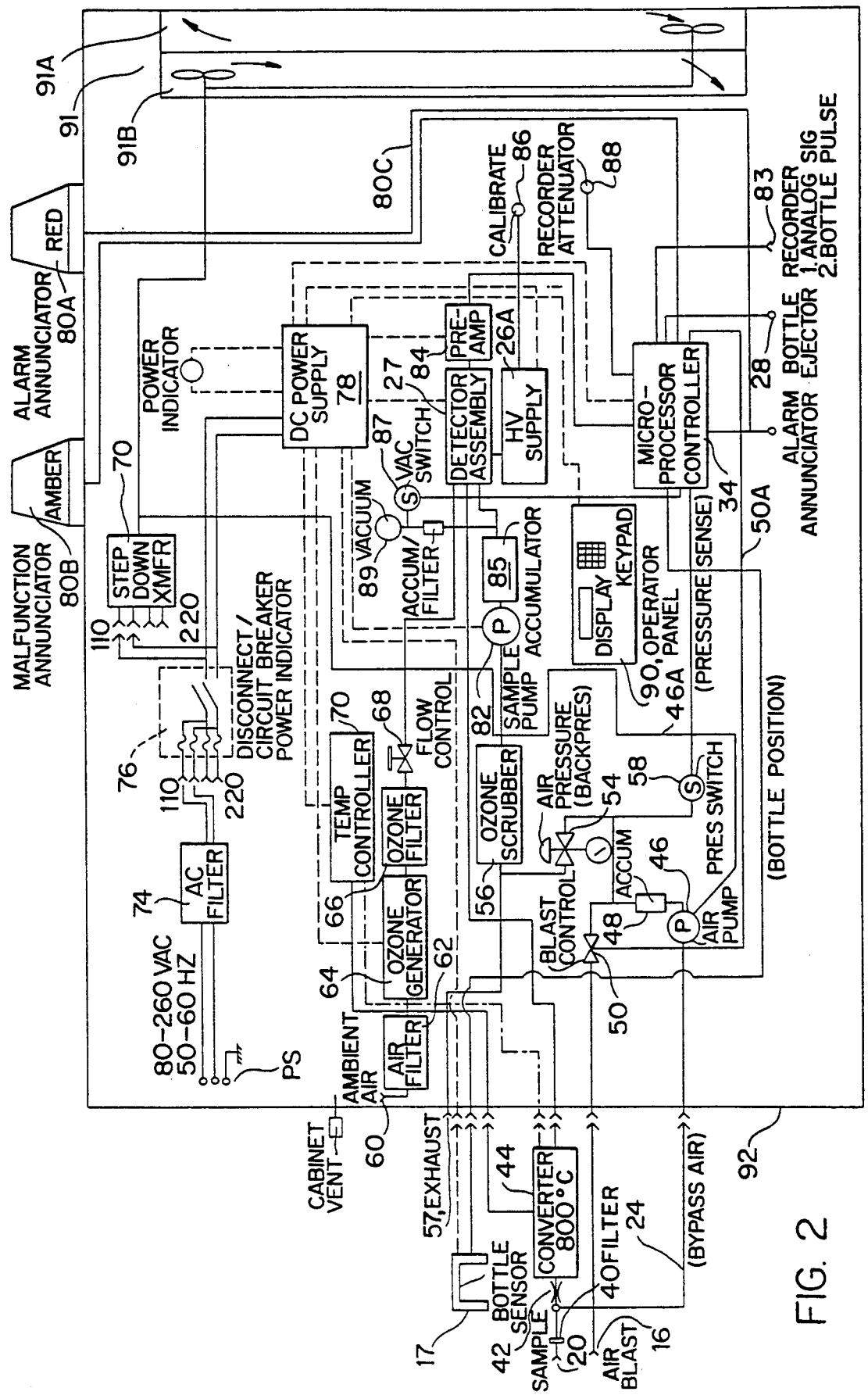

FIG. 1A is a schematic block diagram of a system similar to FIG. 1 with two test stations and detection heads;

Referring to FIG. 2 there is illustrated a specific embodiment of a nitrogen compound detector system for use with the sampling and analyzing system of FIG. 1 wherein like reference numerals refer to like parts. As illustrated, a nozzle 16 is provided for generating an air blast which passes into a container (not shown) being inspected. The air passing through nozzle 16 may be heated or unheated it being advantageous to heat the air for some applications. Juxtaposed to the nozzle 16 is sample inlet tube 20 including a filter 40 at the output thereof for filtering out particles from the sample. Suction is provided to tube 20 from the suction side of pump 82 connected through an analyzer 27.

A portion of the sample (for example, 90–95% of a total sample flow of about 6000 c.c. per minute), as described in connection with FIG. 1, is diverted through a bypass line 24 by means of connection to the suction side of a pump 46. Pump 46 recirculates the air through an accumulator 48, a normally open blast control valve 50, and back to the air blast output nozzle 16. A backpressure regulator 54 helps control pressure of the air blast through nozzle 16 and vents excess air to exhaust 57. Blast control valve 50 receives control signals through line 50A from microprocessor controller 34 to normally maintain the valve open to permit the flow of air to the nozzle.

Electrical power is provided to pump 46 via line 46A coupled to the output of circuit breaker 76 which is in turn coupled to the output of AC filter 74 and AC power supply PS.

The detector assembly 27 in the embodiment of FIG. 2 is an analyzer which detects the residue of selected compounds such as nitrogen containing compounds in the containers being inspected by means of a method of chemiluminescence. This type of detector is generally known and includes a chamber for mixing ozone with nitric oxide, or with other compounds which react with ozone, in order to allow them to react, a radiation-transmissive element (with appropriate filter), and a radiation detector to detect chemiluminescence from the products of reaction. For example, when NO, produced from heating nitrogen compounds (such as ammonia) in the presence of an oxidant (e.g. oxygen in air), chemically reacts with the ozone, characteristic light emission is given off at predetermined wavelengths such as wavelengths in the range of about 0.6 to 2.8 microns. Selected portions of the emitted radiation of chemiluminescence, and its intensity, can be detected by a photomultiplier tube.

Accordingly, in the system of FIG. 2 ambient air is drawn in through intake 60 and air filter 62 to an ozone generator 64. Ozone is generated therein, as by electrical discharge into air, and is output through ozone filter 66 and flow control valve 68 to the detector assembly 27 wherein it is mixed with samples from containers input through intake tube 20, filter 40, flow restrictor 42, and converter 44. The sample from intake tube 20 is passed through a converter 44, such as an electrically-heated nickel tube, in which the temperature is raised to approximately 800° C. to 900° C. before being input to detector assembly 27. Temperatures in the range of 400° C. to 1400° C. may also be acceptable. When nitrogen-containing compounds such as ammonia are so heated, NO (nitric oxide) is produced, and the nitric oxide is supplied to the chamber of the detector assembly 27. Compounds other than NO which may react with $O_3$ and chemiluminescence may also be produced in converter 44 e.g., organic compounds derived from heating of gasoline or cleaning residue.

A temperature controller 70 supplied with electrical power through a transformer 72 is used to control the temperature of converter 44.

The samples in the detector assembly 27 after passage through its chamber are output through an accumulator 85 and pump 82 to an ozone scrubber 56, and to an exhaust output 57 in order to clear the residue detector for the next sample from the next container moving along the conveyor 10 of FIG. 1. (As indicated above, an (optional) fan, not shown in FIG. 2, may be employed to help clear any remaining sample cloud from near the sample inlet tube 20.) Outputs from detector assembly 27 relating to the results of the tests are output through a preamp 84 to microprocessor 34 which feeds this information in an appropriate manner to a recorder 83. The recorder 83 is preferably a conventional strip recorder, or the like, which displays signal amplitude vs. time of the sample being analyzed.

The microprocessor 34 may be programmed to recognize, as a "hit" or the detection of a specific residue, a signal peak from a photodetector of the detector assembly 27 which is present in a predetermined time interval (based on the sensed arrival of a container at the test station) and whose slope and amplitude reach predetermined magnitudes and thereafter maintain such levels for a prescribed duration.

The microprocessor controller 34 also has an output to a bottle ejector 28 to reject contaminated bottles and separate them from bottles en route to a washer.

A calibration terminal 86 is provided for residue analyzer 27 for adjusting the high voltage supply 26A associated with the detector assembly. Also provided is a recorder attenuator input terminal 88 connected to the microprocessor controller 34 for adjusting the operation of the recorder. Detector assembly 27 receives electrical power from the high voltage supply 26A.

Additional controls include operator panel 90 including a key pad and display section permitting an operator to control the operation of the detector assembly 27 in an appropriate fashion.

DC power is supplied to all appropriate components through DC power supply 78 coupled to the output of power supply PS.

An optional alarm enunciator 80A is provided for signaling an operator of the presence of a contaminated container. Alarm enunciator 80A is coupled to the output of microprocessor controller 34 via output control line 80C. A malfunction alarm 80B is also coupled to microprocessor controller 34 for receiving fault or malfunction signals such as from pressure switch 58 or vacuum switch 87 when pressures are outside of certain predetermined limits.

Other safety devices may be provided such as vacuum gauge 89, and back pressure control valve 54 for ensuring proper operation of the system.

Most components of the entire system of FIG. 2 are preferably enclosed in a rust-proof, stainless steel cabinet 92. The cabinet is cooled by a counter-flow heat exchanger 91 having hermetically separated sections 91A and 91B in which counter air flow is provided by appropriate fans.

Figure 3:
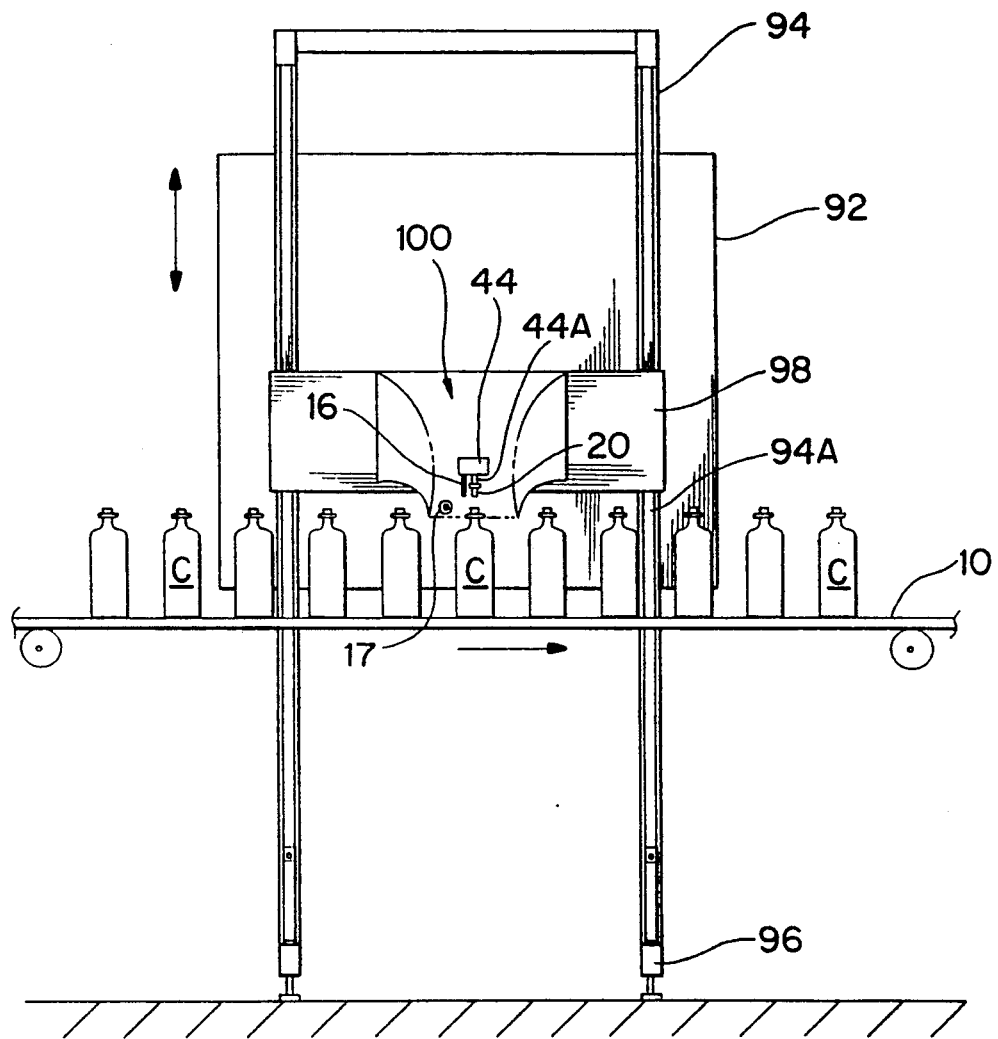

The system illustrated in FIG. 2 is housed within an apparatus illustrated in FIG. 3 which generally includes a stainless steel rectangular cabinet 92 for enclosing the majority of the components of FIG. 2 in a hermetically sealed environment. The rear of cabinet 92 has appropriate doors and access panels for accessing the components of the system when repairs or adjustments are needed. Cabinet 92 is mounted on a rectangular frame 94 which is supported on a leg assembly 96. Both the front and back surfaces of support frame 94 are provided with tracks or slots 94A. The tracks 94A on the back side of frame 94 are provided to enable cabinet 92 to be adjusted in a vertical direction to accommodate conveyors of different heights. A crossbar support 98 is adapted to slide up and down in tracks 94A on the front side of support 94. Converter 44 for heating the sample portion evacuated for analysis is cantilevered to crossbar support 98. A shroud or hood 100 is also cantilevered to crossbar 98 and is provided to enclose converter 44 and to define a tunnel over the sampling region of the test station through which containers C move along conveyor 10. Further details of this shroud are illustrated in FIGS. 4-6 to be described hereinafter.

The mounting of crossbar support 98 in tracks 94A facilitates vertical adjustment of shroud 100 and the air injection nozzle and sampling tube 20 to accommodate different size containers C thereunder.

Figure 4:
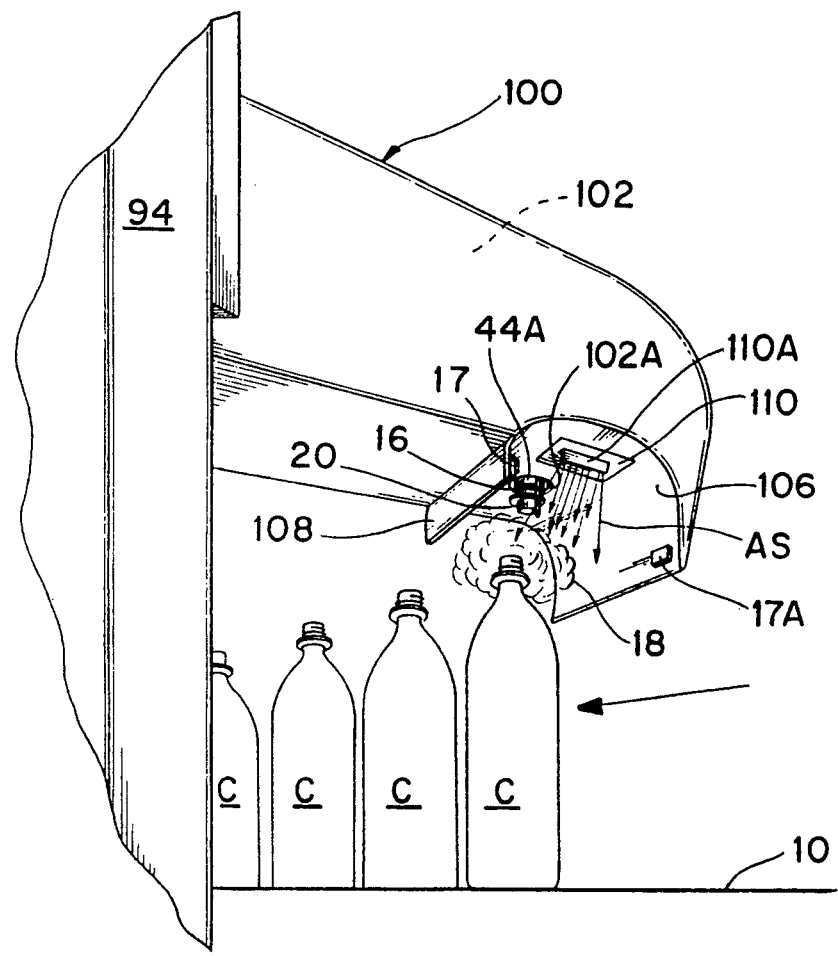
Figure 5:
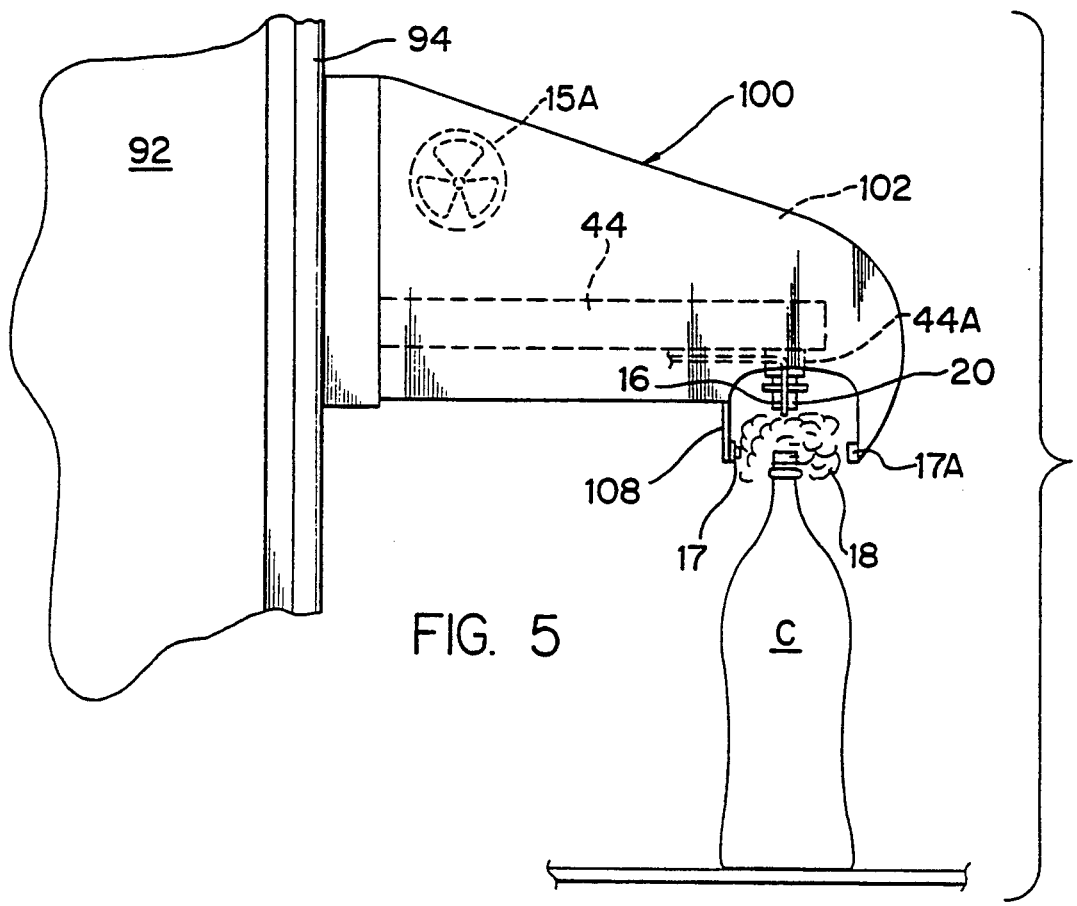
Figure 6:
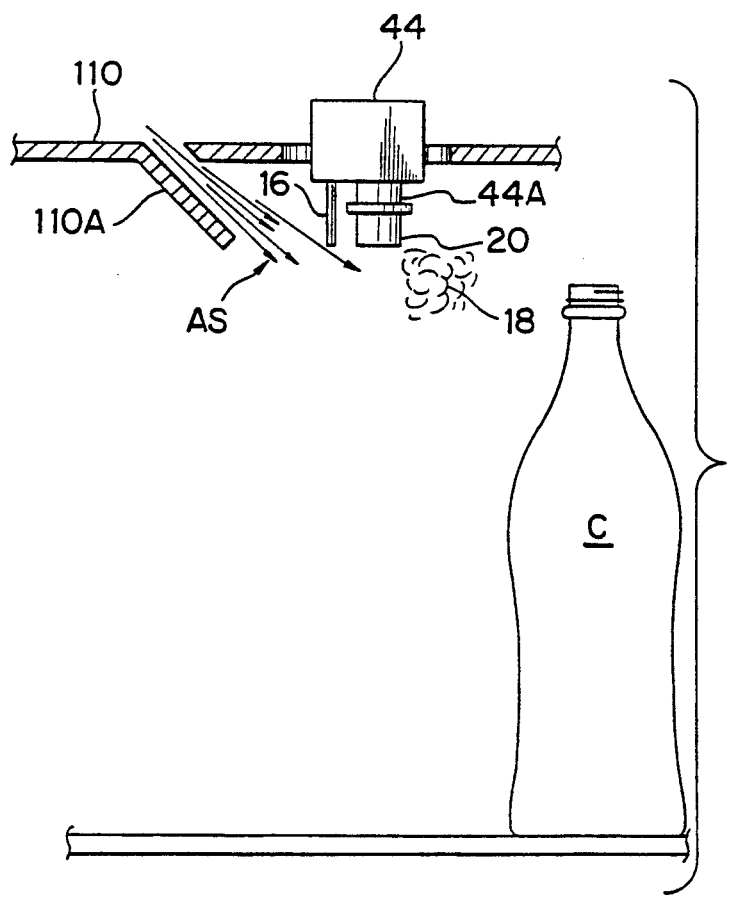

Referring in detail to FIGS. 4-6 it can be seen that the shroud 100 includes an upper chamber 102 for housing converter 44 and a fan 15A. An aperture 102A is provided in the bottom of chamber 102 of shroud 100. A tube 44A extends from the bottom of converter 44 and connects to sample intake tube 20 which extends through aperture 102A. Also extending through aperture 102A, and being disposed adjacent to sample tube 20, is air nozzle 16. The fan 15A within chamber 102 pressurizes the entire chamber to keep material from sample cloud 18 and any other ambient materials from entering aperture 102A. Therefore, it keeps the region around converter 44 clean.

The air generated from fan 15A is also useful for directing an air stream through a louvered plate 110, having at least one louver 110A therein, through the sampling region above the containers being tested. The effect of this air stream is best illustrated in FIG. 6 wherein it can be seen that the stream of air AS passing through louver 110A blows remnants of sample cloud 18 out of the sampling region at the test station toward the downstream side of the conveyor 10. Accordingly, the air stream AS generated by fan 15A and associated louver plate 110 clears out the sampling region continuously so that successive containers are not contaminated with samples from previously inspected containers.

Louver plate 110 is reversible in an aperture defined by the bottom wall 106 of shroud 100 so that for a direction of movement of conveyor 10 opposite to that of FIG. 6, plate 110 may be simply reversed pointing louver 110A in the opposite direction, and directing an air stream in that direction toward the downstream end of the conveyor.

Referring in more detail to FIGS. 4 and 5 the bottom of the shroud 100 includes a curved bottom wall including curved portion 106 which together with a baffle 108 forms a curved hood or tunnel over the sampling region at the test station. The purpose of this tunnel or hood is to contain sample cloud 18 within reasonable limits so that the air stream generated by fan 15A and louver plate 110 is directed into an aerodynamic enclosure which assists in the efficient removal of remnants of any sample cloud 18 from the test area. The containment of the sampling region within this tunnel-like structure also enhances the efficiency of sampling through sample tube 20.

The bottle position detector previously described with respect to FIG. 1 is illustrated as element 17 in FIG. 5 and is mounted on the bottom of baffle 108. Element 17 includes a juxtaposed light source and photodetector aligned with a reflector 17A mounted on opposed wall 106 of the shroud. Thus, it can be seen that a container C passing into the tunnel defined by surfaces 106 and baffle 108 will break the light beam and generate a signal to indicate the presence of the container at the test station.

The invention being thus described, it will be obvious that the same may be varied in many ways. For example, other forms of high speed analyzers, such as electron capture detectors or photoionization detectors, may be suitable in place of the chemiluminescence analyzer described with reference to FIG. 2.

One preferred detector is a pulsed fluorescent gas analyzer of the type described in U.S. Pat. No. 3,845,309

(Helm et al), whose disclosure is incorporated herein by reference to that patent. In such analyzers gaseous samples drawn into a chamber and illuminated by radiant energy from a flash-tube fluoresce and emit radiation which is detected by a photodetector. It has been found that an analyzer of the type referred to in the '309 patent, such as a Model 43 Pulsed Fluorescent $SO_2$ Analyzer available from Thermo Environment Instruments, Inc. of Franklin, Massachusetts, when modified by removal of bandpass filters, becomes a highly sensitive detector of certain hydrocarbons such as polycyclic aromatic hydrocarbons present in gasoline and other petroleum products. The modified fluorescent gas analyzer may be used as the residue analyzer 26 in the systems of FIG. 1 and FIG. 2 (in the latter system no ozone generator 64 or ozone-handling components would be needed, and preferably a converter 44 would also be unnecessary.

Also the sample sucked into the tube 20 may be separated into two or more streams and input to a plurality of analyzers 27. Consequently, each analyzer 26 (FIG. 1) could be used to detect different types of contaminants. It is also possible to use totally diverse types of analyzers than analyzer 27 (FIG. 2) which pretreats the sample in converter 44. In that case part of the sample would be routed to the diverse type of analyzer and part to converter 44.

In addition the materials to be inspected are not limited to substances in containers. For example, the method and system of the present invention could be used to detect volatiles adsorbed in shredded strips or flakes of resins, or plastic stock to be recycled for manufacturing new plastic beverage bottles. This shredded or flaked plastic stock could be placed directly on a conveyor belt 10 and passed through test station 12 of FIG. 1; or the plastic stock could be placed in baskets, buckets or other types of containers disposed thereon and inspected in batches.

Other materials which could be inspected according to the method and system of the invention include various foodstuffs such as fish being monitored for amines, pharmaceutical products and herbicides being checked for reagents, rubber products such as tires being monitored for chemicals such as blowing agents, web materials such as paper in a paper mill being checked for acids, and even clothing worn by persons being inspected for volatile compounds such as explosives or drugs. Such materials may be inspected while passing through a test station on a conveyor, either within open containers or in the absence of containers. In the latter case high flow rates and/or heating of the compressed air or other fluid directed at the material by the nozzle 16 may be in order to obtain desired samples of the volatile substances to be detected.

Still further the bottles being tested may be new bottles that have never been filled with a beverage. Thus, new bottles could be tested for excessive acid aldehyde content, which may be a byproduct of the manufacturing process.

Such variations are not to be regarded as a departure from the spirit and scope of the invention, and all such modifications as would be obvious to one skilled in the art are intended to be included within the scope of the following claims.

What is claimed is:

1. A system for sampling and determining a presence of certain residues in containers comprising:

means for injecting fluid into openings in said containers in order to displace at least a portion of contents thereof to form a sample cloud at regions outside of the containers;

means for evacuating a sample of said portion of the contents of each container so displaced by applying suction to the sample cloud; and means for supporting said means for evacuating outside of said containers in spaced relationship from the openings thereof; and means for analyzing the sample evacuated to determine the presence or absence of the certain residues therein.

2. The system of claim 1 further including means for moving said container seriatim past a test station and control means constraining said means for injecting to continuously inject said fluid at said test station, and constraining said means for evacuating to continuously apply suction as the containers move through said test station.

3. The system of claim 1 further including control means for initiating the injection of the fluid before initiating the evacuation of the fluid.

4. The system of claim 3 wherein the control means constrains the operation of the injecting means and evacuating means to overlap in time.

5. The system of claim 3 wherein control means terminates the operation of the means for injecting before initiation of the means for evacuating.

6. The system of claim 1 wherein the control means synchronizes the injecting and evacuating means so that injection and evacuation occur simultaneously for the same duration.

7. The system of claim 6 wherein the fluid injected is compressed air.

8. The system of claim 7 wherein the fluid injected is compressed air.

9. The system of claim 4, wherein the fluid injected is compressed air.

10. The system of claim 3 wherein the fluid injected is compressed air.

11. The system of claim 1 wherein the fluid injected is compressed air.

12. A system for sampling and determining a presence of certain residues in containers moving seriatim past a test station comprising:

means for injecting fluid into each container as it reaches said test station in order to displace at least a portion of contents thereof to form a sample cloud at regions outside of the containers;

means for evacuating a sample of the container contents so displaced by applying suction to the sample cloud;

means for diverting a first portion of the sample; and means for analyzing a second portion of the sample evacuated to determine the presence or absence of the certain residues therein.

13. The system of claim 12 further including control means constraining said means for injecting to continuously inject said fluid at said test station, and constraining said means for evacuating to continuously apply suction as the containers move through said test station.

14. The system of claim 12 further including means for recirculating said diverted first portion into successive containers to arrive at the test station.

15. The system of claim 14 further including control means for initiating the injection of the fluid before initiating the evacuation of the fluid.

16. The system of claim 15 wherein the control means constrains the operation of the injecting means and evacuating means to overlap in time.

17. The system of claim 15 wherein control means terminates the operation of the means for injecting before initiation of the means for evacuating.

18. The system of claim 12 wherein the control means synchronizes the injecting and evacuating means so that injection and evacuation occur simultaneously for the same duration.

19. The system of claim 12 further including means for directing a stream of air into a region of the test station as each container leaves the test station to remove any residual cloud of that container's contents before successive containers to be tested arrive at the test station.

20. The system of claim 12 wherein said means for analyzing comprises:
  means for heating the sample evacuated to about 800° to 1400° C.;
  means for mixing the heated sample with ozone to cause a chemical reaction therewith in order to generate chemiluminescence of the heated sample; and
  means for optically analyzing radiation emitted by chemiluminescence to determine the presence or absence of said certain residues.

21. The system of claim 1 wherein said means for analyzing comprises:
  means for heating the sample evacuated to about 800° to 1400° C.;
  means for mixing the heated sample with ozone to cause a chemical reaction therewith in order to generate chemiluminescence of the heated sample; and
  means for optically analyzing radiation emitted by chemiluminescence to determine the presence or absence of said certain residues.

22. Apparatus for sampling and determining a presence of certain residues containers moving through a test station comprising:
  means for injecting fluid into openings in said containers in order to displace at least a portion of contents thereof;
  means for evacuating a sample of said portion of the container contents so displaced by applying suction thereto;
  means for supporting both the means for injecting and evacuating outside of said containers in spaced relationship from the openings thereof, said means for injecting displacing said portion of the contents to form a sample cloud at regions outside of the containers adjacent the openings thereof, and said means for evacuating applying suction to the sample cloud in said regions outside of said containers;
  means for directing a stream of air into said regions as each container leaves the test station to remove any residual portions of the sample cloud of that container's contents before successive containers to be tested arrive at the test station; and
  means for analyzing the sample evacuated to determine the presence or absence of certain residues therein.

23. The apparatus of claim 22 further including a hood disposed over and partially enclosing the test station, said hood having a substantially continuous curved surface defining a tunnel through which said containers may pass, said air-directing means operable to pass an air stream through said tunnel and along said curved surface to remove residual portions of the sample cloud, which have not been evacuated, from the regions at said test station.

24. The apparatus of claim 23 further comprising:
  a shroud enclosing at least a portion of said means for evacuating in an upper portion thereof which defines a substantially closed chamber;
  fan means disposed within said chamber for pressurizing the chamber with air; and
  louver means in the bottom of said chamber for creating said stream of air directed into said region by directing air from said fan means out of said chamber and through said tunnel.

25. The apparatus of claim 24 defining wherein the curved surface the tunnel of said hood is disposed on the bottom of the top portion of said shroud in fluid communication with said louver means.

26. The apparatus of claim 25 wherein said louver means includes a plate removably mounted in an aperture defined by a wall of said chamber and at least one louver for directing the air stream in a first predetermined direction through said tunnel, the louver means being reversible in the aperture in order to facilitate direction of said stream of air through the tunnel in a direction opposite to said first direction.

* * * * *